United States Patent
Alpegiani et al.

Patent Number: 5,580,865
Date of Patent: Dec. 3, 1996

[54] 2,2-DISUBSTITUTED CEPHEM SULPHONES

[75] Inventors: Marco Alpegiani, Milan; Pierluigi Bissolino, S. Giorgio Lomellina; Ettore Perrone; Vincenzo Rizzo, both of Milan, all of Japan

[73] Assignee: Farmitalia Carlo Erba S.r.l., Milan, Italy

[21] Appl. No.: 43,023

[22] Filed: Apr. 5, 1993

[30] Foreign Application Priority Data

Apr. 8, 1992 [GB] United Kingdom ............ 9207715

[51] Int. Cl.$^6$ .................... C07D 501/22; C07D 501/24; A61K 31/545

[52] U.S. Cl. ............. 514/202; 514/200; 514/204; 514/207; 514/208; 514/209; 540/215; 540/222; 540/223; 540/226; 540/228; 540/229; 540/230

[58] Field of Search ................. 540/230, 215, 540/215, 226; 514/202, 200, 208

[56] References Cited

U.S. PATENT DOCUMENTS

| | | | |
|---|---|---|---|
| 4,547,371 | 10/1985 | Doherty et al. | 540/230 |
| 5,077,286 | 12/1991 | Bissolino et al. | 540/230 |
| 5,348,952 | 9/1994 | Bissolino et al. | 540/226 |

FOREIGN PATENT DOCUMENTS

| | | |
|---|---|---|
| 0337704 | 10/1989 | European Pat. Off. . |
| 2250759 | 6/1975 | France . |
| 2254575 | 7/1975 | France . |
| PCT/EP90/ 02189 | 6/1991 | WIPO . |
| WO91/09036 | 6/1991 | WIPO . |

OTHER PUBLICATIONS

Chemical Abstracts, vol. 82, No. 7, Feb. 17, 1975, AN 43443g, p. 444, JP-A-7 448 690.
Chemical & Pharmaceutical Bulletin, vol. 23, No. 11, Nov. 1975, pp. 2507-2517, Akira Yoshida, et al.

Primary Examiner—John M. Ford
Attorney, Agent, or Firm—Oblon, Spivak, McClelland, Maier & Neustadt, P.C.

[57] ABSTRACT

The present invention provides cephalosporin sulphones or formula (I), and pharmaceutically or veterinarily acceptable salts thereof;

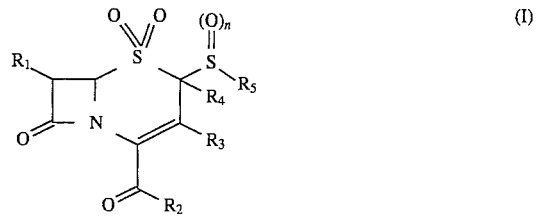

wherein n is zero, one or two;

$R_1$ is hydrogen, halogen or an optionally substituted $C_1$–$C_4$ alkyl, $C_2$–$C_4$ alkenyl, $C_1$–$C_4$ alkoxy, $C_1$–$C_4$ alkylthio or $C_1$–$C_4$ carboxamido group;

$R_2$ is hydrogen or an optionally substituted $C_1$–$C_8$ alkyl, $C_6$–$C_{10}$ aryl, $C_2$–$C_5$ alkenyl or $C_3$–$C_6$ cycloalkyl group;

$R_3$ is hydrogen or acetoxymethyl, methoxymethyl, methyl or an optionally substituted heterocyclylthiomethyl group;

$R_4$ is an optionally substituted $C_1$–$C_8$ alkyl, $C_2$–$C_6$ alkenyl, aryl($C_1$–$C_8$)alkyl or heterocyclyl($C_1$–$C_8$)alkyl group; and $R_5$ is an optionally substituted $C_6$–$C_{10}$ aryl or a heterocyclyl group.

The compounds of formula I and the pharmaceutically and veterinarily acceptable salts thereof are elastase inhibitors.

6 Claims, No Drawings

2,2-DISUBSTITUTED CEPHEM SULPHONES

The present invention relates to new cephalosporin sulphones, their preparation and to pharmaceutical and veterinary compositions containing them.

The compounds disclosed in the present invention feature the simultaneous presence on the cephem skeleton of an acyl group at C-4 and a sulphenyl, sulphinyl or sulphonyl group and an alkyl group at C-2.

According to the invention there are provided cephalosporin sulphones of formula (I) and the pharmaceutically and veterinarily acceptable salts thereof:

(I)

wherein n is zero, one or two:

$R_1$ is hydrogen, halogen or an optionally substituted $C_1$–$C_4$ alkyl, $C_2$–$C_4$ alkenyl, $C_1$–$C_4$ alkoxy, $C_1$–$C_4$ alkylthio or $C_1$–$C_4$ carboxamido group;

$R_2$ is hydrogen or an optionally substituted $C_1$–$C_8$ alkyl, $C_6$–$C_{10}$ aryl, $C_2$–$C_5$ alkenyl or $C_3$–$C_6$ cycloalkyl group;

$R_3$ is hydrogen or acetoxymethyl, methoxymethyl, methyl or an optionally substituted heterocyclylthiomethyl group;

$R_4$ is an optionally substituted $C_1$–$C_8$ alkyl, $C_2$–$C_6$ alkenyl, aryl($C_1$–$C_8$)alkyl or heterocyclyl($C_1$–$C_8$)alkyl group; and $R_5$ is an optionally substituted $C_6$–$C_{10}$ aryl or heterocyclyl group.

A heterocyclyl($C_1$–$C_8$)alkyl group is preferably a heterocyclylmethyl group.

The term heterocyclyl group preferably refers to a 5- or 6-membered, saturated or unsaturated, heterocyclic ring containing at least one heteroatom chosen from O, S and N, which is optionally fused to an aryl group. Such a group may be The alkyl, alkenyl, alkoxy, alkylthio and carboxamido groups may be straight or branched chain groups. The above said alkyl, alkenyl, alkoxy, alkylthio, aryl, aralkyl, heterocyclyl, heterocyclylalkyl, cycloalkyl and heterocyclylthiomethyl groups can be either unsubstituted or substituted by one or more substituents selected from:

$C_1$–$C_5$ alkyl, $C_2$–$C_5$ alkenyl, phenyl, benzyl or $C_3$–$C_6$ cycloalkyl;

halo;

protected hydroxy;

oxo;

cyano;

nitro;

azido;

protected amino or —$NHR^I$; or —$NR^IR^{II}$ wherein $R^I$ and $R^{II}$, being the same or different, are hydrogen atom or $C_1$–$C_5$ alkyl, $C_2$–$C_5$ alkenyl, phenyl, benzhydryl or benzyl, or $R^I$ and $R^{II}$ taken together with the nitrogen atom constitute a succinimido or phthalimido group;

protected carboxy;

—$OR^I$ or —$OCH_2CH_2OR^I$ wherein $R^I$ is as defined above;

—$SR^I$ wherein $R^I$ is as defined above;

—$S(O)R^I$ wherein $R^I$ is as defined above;

—$S(O)_2R^I$ wherein $R^I$ is as defined above;

a group of formula $(CH_2)_m$—$COOR^I$, —$COOR^I$, —$COO(CH_2)_mCOOR^I$, —$S(CH_2)_mCOOR^I$ or —$O(CH_2)_mCOOR^I$ wherein $R^I$ is as defined above and m is 1, 2, 3 or 4;

—$COCH_2COOR^I$ wherein $R^I$ is as defined above or $COR^{III}$ wherein $R^{III}$ is either $R^I$ as defined above or fluoromethyl, trifluoromethyl or chloromethyl;

—$OCOR^{III}$ wherein $R^{III}$ is as defined above;

—$CONH_2$, or —$CONHR^I$ or —$CONHCH_2COOR^I$ wherein $R^I$ is as defined above or —$CONHCH_2COOH$;

sulpho ($SO_3H$);

—$NHCOR^I$ wherein $R^I$ is as defined above;

—$NHS(O)^2R^I$ wherein $R^I$ is as defined above; and guanidino (—$NHC(=NH)NH_2$).

Halogen is preferably fluorine, chlorine or bromine. An aryl($C_1$–$C_8$)alkyl group is preferably an arylmethyl or arylethyl group. An aryl group is preferably a phenyl or naphthyl group unsubstituted or substituted by one or more of the afore-mentioned substituents.

A $C_1$–$C_8$ alkyl group is preferably a $C_1$–$C_5$ alkyl group such as a $C_1$–$C_4$ alkyl group. The alkyl group may be methyl, ethyl, propyl, n-butyl, tert-butyl, isopropyl or amyl. The alkyl moiety of the $C_1$–$C_4$ alkoxy, $C_1$–$C_4$ alkylthio and $C_1$–$C_4$ carboxamido groups typically is a methyl, ethyl, propyl, n-butyl, tertbutyl or isopropyl group.

A $C_2$–$C_6$ alkenyl group is preferably a $C_2$–$C_5$ alkenyl group such as a $C_2$–$C_4$ alkenyl group. The alkenyl group may be vinyl, allyl, 1-propenyl, 2-methyl-1-propenyl, 1-methyl-1-propenyl or 1-methylethenyl.

A $C_3$–$C_6$ cycloalkyl group is preferably cyclopentyl or cyclohexyl.

A preferred carboxy protecting group is tert-butyl, benzyl, 4-methoxybenzyl, 2,4-dimethoxybenzyl, benzhydryl, 4-nitro-benzyl, allyl, tetrahydropyranyl, acetoxymethyl, 1-acetoxyethyl, 5-methyl-1,3-dioxolen-2-on-4-yl, pivaloyloxymethyl, 1-phenoxyethyl, 2-trimethylsilyl-1-ethyl, 2-iodoethyl, methoxymethyl, trimethylsilyl, tert-butyldiphenylsilyl or tert-butyldimethylsilyl.

A preferred hydroxy protecting group is formyl, acetyl, butyryl, chloroacetyl, trichloroacetyl, benzhydryl, pyranyl, trityl, trifluoroacetyl, methoxymethyl, methoxyethoxymethyl, trimethylsilyl, tert-butyldimethylsilyl, tert-butyldiphenylsilyl, benzoyl, allyloxycarbonyl, p-nitrobenzyloxycarbonyl, trichloroethoxycarbonyl, p-methoxbenzyloxycarhonyl or benzyloxycarhonyl.

A preferred amino protecting group is formyl, acetyl, chloroacetyl, trichloroacetyl, trityl, trifluoroacetyl, allyloxycarbonyl, p-nitrobenzyloxycarbonyl, benzyloxycarbonyl, trichloroethoxycarbonyl, p-methoxybenzyloxycarbonyl or tert-butoxycarbonyl.

The present invention provides the salts of those compounds of formula (I) that have salt-forming groups, especially the salts of the compounds having a carboxylic group or a basic group (e.g. an amino or guanidino group). The salts are especially tolerable salts, for example alkali metal and alkaline earth metal salts (e.g. sodium, potassium, lithium, calcium and magnesium salts), ammonium salts and salts with an appropriate organic amine or amino acid (e.g. arginine, procaine salts), and the addition salts formed with suitable organic or inorganic acids, for example hydrochloric acid, sulphuric acid, carboxylic and sulphonic acids (e.g. acetic, trifluoroacetic, p-toluensulphonic acid).

The present invention encompasses all the possible stereoisomers and tautomers, as well as their racemic or optically active mixtures.

Particularly preferred compounds are those represented by formula (I')

wherein n is 0, 1 or 2;

$R_1$ is hydrogen, fluorine, chlorine, methyl, ethyl, propyl, iso-propyl, n-butyl, 2-methyl-1-propyl, allyl, methallyl, crotyl, 3-methyl-2-buten-1-yl, methoxy, ethoxy, propoxy, iso-propoxy, n-butoxy, methylthio, ethylthio, propylthio, isopropylthio, n-butylthio, formamido, acetamido or propionamido;

$R_2$ is hydrogen, methyl, ethyl, propyl, iso-propyl, n-butyl, 2-methyl-1-propyl, neo-pentyl, 1,1-dimethylpropyl, vinyl, 1-propenyl, 2-phenyl-2-propyl, 2-methyl-1-propenyl, benzyl, cyclopropyl, cyclopentyl, cyclohexyl, phenyl, p-tert-butylphenyl, p-carboxyphenyl or p-sulphophenyl;

$R_3$ is hydrogen, methyl, methoxymethyl, acetoxymethyl or a group —$CH_2S$-Het, wherein Het is a heterocyclic group:

wherein $R^I$ is as defined above, typically hydrogen, methyl, allyl or benzyl, or a hydroxy protecting group and $R^{IV}$ is as defined for $R^I$, typically hydrogen, methyl, allyl or benzyl or a carboxy protecting group;

$R_4$ is methyl, ethyl, methallyl, crotyl, methoxycarbonylmethyl, tert-butoxycarbonylmethyl, carboxymethyl, cyanomethyl, acetonyl, methoxymethyl, methoxyethoxymethyl, acetoxymethyl, benzyl, 4-methoxybenzyl, 4-nitrobenzyl or benzhydryl or a group —$CH_2$—⟨phenyl⟩—$COOR^{IV}$ wherein $R^{IV}$ is as defined above;

$R^5$ is phenyl, 4-carboxyphenyl or a heterocyclyc ring:

wherein $R^V$ is hydrogen, methyl, ethyl, propyl, phenyl, benzyl, carboxymethyl, 2-carboxyethyl, 3-carboxypropyl, 3-benzhydryloxycarbonylpropyl, 2-sulphoethyl, 2,2-dimethylaminoethyl;

wherein X is oxygen, sulphur, or $NR^{VII}$ wherein $R^{VII}$ is hydrogen, methyl, phenyl, carboxymethyl;

wherein $R^I$ is as defined above;

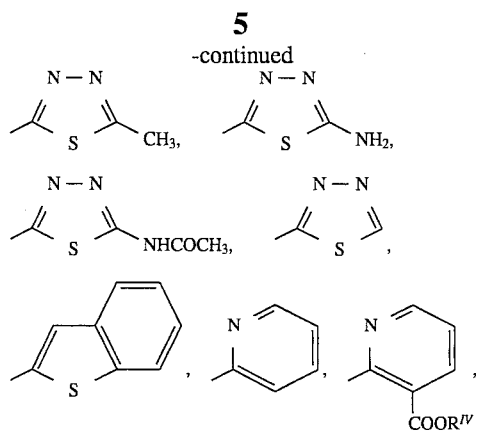
wherein
R$^{IV}$ is as defined above;
and the pharmaceutical and veterinary acceptable salts thereof and all the possible stereoisomers and tautomers.
Specific examples of the preferred compounds are listed in Table I.

TABLE I

| Comp. | n | $R_1$ | $R_2$ | $R_3$ | $R_4$ | $R_5$ |
|---|---|---|---|---|---|---|
| 1 | 0 | Cl | t-Bu | $CH_3$ | $CH_3$ | 1-methyl-1,2,4-triazol-3-yl |
| 2 | " | " | phenyl | " | " | " |
| 3 | " | " | 4-t-$C_4H_9$-phenyl | " | " | " |
| 4 | " | " | –$CH_2$–phenyl | " | " | " |
| 5 | " | $OCH_3$ | t-Bu | " | " | " |
| 6 | " | " | " | " | –$CH_2$–(4-$NO_2$-phenyl) | " |
| 7 | " | " | " | " | –$CH_2$–CH=$CH_2$ | " |
| 8 | " | " | " | " | –$CH_2COOBu^t$ | " |
| 9 | " | " | " | " | –$CH_2COOH$ | " |

TABLE I-continued

| Comp. | n | $R_1$ | $R_2$ | $R_3$ | $R_4$ | $R_5$ |
|---|---|---|---|---|---|---|
| 10 | " | " | " | " | $-CH_2-C_6H_5$ | $CH_3-N\overset{N}{=}\underset{CH_3}{\overset{OCHPh_2}{\diagdown}}\cdots$ |
| 11 | " | " | " | " | $CH_3$ | $CH_3-N\overset{N}{=}\underset{CH_3}{\overset{OH}{\diagdown}}\cdots$ |
| 12 | " | " | " | " | " | $\underset{CH_3}{N=N}\underset{\underset{CH_3}{|}}{N}\cdots$ |
| 13 | 0 | $OCH_3$ | $C_6H_5$ | $CH_3$ | $CH_3$ | $CH_3-N\overset{N}{=}\underset{CH_3}{\overset{OCHPh_2}{\diagdown}}\cdots$ |
| 14 | " | " | t-Bu | $CH_3$ | $-CH_2-C_6H_5$ | |
| 15 | " | " | " | " | $CH_3$ | $CH_3-N\overset{N}{=}\underset{CH_3}{\overset{OCH_3}{\diagdown}}\cdots$ |

TABLE I-continued
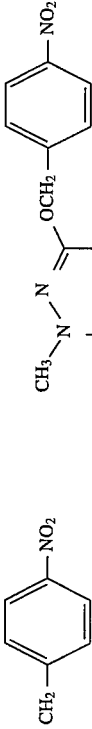
| Comp. | n | $R_1$ | $R_2$ | $R_3$ | $R_4$ | $R_5$ |
|---|---|---|---|---|---|---|
| 16 | " | " | " | " |  |  |
| 17 | " | " |  | " | $CH_3$ | 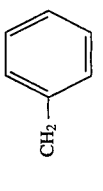 |
| 18 | " | " | " | " | 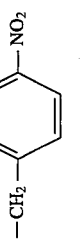 | " |
| 19 | " | " | t-Bu | " |  | " |
| 20 | " | " | " | " | $-CH_2COOBu^t$ | " |
| 21 | " | " | " | " | $CH_3$ |  |
| 22 | " | " | " | $-CH_2OCOCH_3$ | " | " |
| 23 | " | " | " | $-CH_2OCH_3$ | " | " |

TABLE I-continued

| Comp. | n | $R_1$ | $R_2$ | $R_3$ | $R_4$ | $R_5$ |
|---|---|---|---|---|---|---|
| 24 | 0 | $OCH_3$ | t-Bu | $CH_3$ | $CH_2CH=CH_2$ | $CH_3\text{-}N\text{-}N=N\text{-}N(CH_3)\text{-}C(=N)\text{-}C(=O)\text{-}OCHPh_2$ (methyltetrazolyl-glyoxylate-OCHPh$_2$) |
| 25 | " | " | cyclopentyl | " | $CH_3$ | " |
| 26 | " | " | cyclohexyl | " | " | " |
| 27 | " | " | $-CH_2-Bu^t$ | " | " | " |
| 28 | " | " | t-Bu | $-CH_2-S-$(methyltetrazolyl) | " | $CH_3\text{-}N\text{-}N=N\text{-}N(CH_3)\text{-}C(=N)\text{-}C(OH)=$ |
| 29 | " | " | " | $CH_2OCH_3$ | $-CH_2-C_6H_4-COO\text{-}t\text{-}Bu$ (para) | (methyltetrazolyl-glyoxylate) |
| 30 | " | " | " | $CH_3$ | $-CH_2-C_6H_4-CO_2CHPh_2$ (para) | " |

TABLE I-continued
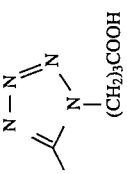
| Comp. | n | $R_1$ | $R_2$ | $R_3$ | $R_4$ | $R_5$ |
|---|---|---|---|---|---|---|
| 31 | " | " | " | " |  | " |
| 32 | " | " | " | " |  |  |
| 33 | " | " | " | " | $CH_3$ | 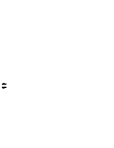 |
| 34 | " | " | " | " | " |  |
| 35 | 0 | $OCH_3$ | t-Bu | $CH_3$ |  | 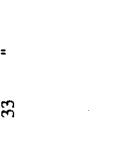 |
| 36 | 1 | " | " | " | " | " |
| 37 | 2 | " | " | " | " | " |
| 38 | 0 | " | " | " | $CH_3$ | " |
| 39 | 1 | " | " | " | " |  |

TABLE I-continued
| Comp. | n | $R_1$ | $R_2$ | $R_3$ | $R_4$ | $R_5$ |
|---|---|---|---|---|---|---|
| 40 | 2 | = | = | = | = |  |
| 41 | 0 | = | = | = |  (4-COOH benzyl) | = |
| 42 | 1 | = | = | = | = | = |
| 43 | 2 | = | = | = | = | = |
| 44 | 1 | = | = | = | $CH_3$ |  |
| 45 | 1 | = | = | = |  (benzyl) | = |
| 46 | 0 | $OCH_3$ | t-Bu | $CH_3$ |  (benzyl) | = |
| 47 | = | $CH_2CH=CH_2$ | = | = | = | = |
| 48 | = | $CH_2CH_2CH_3$ | = | = | = | = |
| 49 | = | = | = | = |  (4-$CO_2H$ benzyl) |  |

TABLE I-continued $$\underset{R_1\text{''}}{\overset{O=S=O}{\underset{O}{\bigvee}}}\overset{R_4}{\underset{R_3}{\overset{S-R_5}{\underset{C-R_2}{\bigvee}}}}^{(O)_n}$$

| Comp. | n | $R_1$ | $R_2$ | $R_3$ | $R_4$ | $R_5$ |
|---|---|---|---|---|---|---|
| 50 | " | $CH_2CH=CH_2$ | " | " | " | ![1-methyl-pyrazol-3-yl group: $\underset{CH_3}{\overset{N=N}{\underset{N}{\bigvee}}}$] |
| 51 | " | $CH_2CH_2CH_3$ | " | " | " | " |
| 52 | " | $CH_2CH_3$ | " | " | " | " |

The present invention relates also to the preparation of cephem sulphones of formula (I). Accordingly, the compounds of the present invention can be prepared by a process which comprises:

(i) reacting a compound of the formula (II)

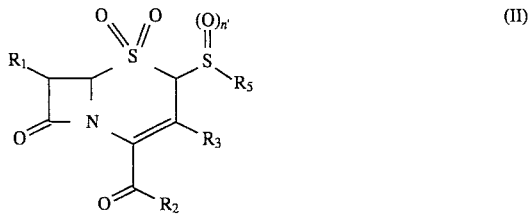

wherein n' is 0, 1 or 2 and $R_1$, $R_2$, $R_3$, $R_4$ and $R_5$ are as defined above, with compounds of formula (III)

L—$R_4$(III)

wherein $R_4$ is as defined above and L is a leaving group;

(ii) if needed, in the case that n defined under formula (I) is of higher value than n' above defined, oxidizing the obtained compounds to compounds of formula (I);

(iii) if desired, converting the resulting compound of formula (I) into a pharmaceutical or veterinarily acceptable salt thereof In step (i) the leaving group L is preferably a halogen atom, preferably chlorine, bromine or iodine, or a $C_1$–$C_3$ alkylsulphonyl residue such as mesyl, triflyl or an arylsulphonyl residue such as tosyl or brosyl. The alkylation reaction can be carried out in a wide range of organic solvents such as dichloromethane, tetrahydrofuran, dioxane, ethyl acetate, chloroform, benzene, carbon tetrachloride, diethyl ether, dimethoxyethane, sulpholane, acetonitrile, N,N-dimethylformamide, N-methylpyrrolidone, dimethylsulphoxide, hexamethylphosphoramide. Reaction temperatures range between –60° C. and +40° C., preferably between –20° C. and room temperature. Said reaction is usually performed in the presence of tertiary organic bases either aliphatic or aromatic or allcyclic such as triethylamine, diisopropylethylamine, aniline, pyridine, lutidine, collidine, quinoline, N-methylmorpholine, N-methylpyrrolidine, diazabicyclooctane (DABCO); or inorganic bases such as alkaline bicarbonates, or carbonates, e.g. sodium bicarbonate, calcium carbonate, cesium carbonate, potassium carbonate. A beneficial effect has often been observed upon addition of alkaline metal salts such as sodium iodide or potassium iodide or heavy metal salts such as silver nitrate, silver perchlorate, silver triflate, copper nitrate, mercury nitrate.

If needed, the oxidation reaction mentioned in step (ii) is performed with organic or inorganic peracids or salts thereof, preferably peracetic acid, metachloroperbenzoic acid, permaleic acid, perphtalic acid, oxone, sodium or potassium persulphate in suitable organic solvents or mixtures of organic solvents with water. Preferred reaction temperatures range between –40° C. and +40° C.

It is understood that in the process above any functional group, if needed or desired can be masked by conventional method and unmasked at the end or when convenient. It is also understood that the groups $R^1$, $R^2$, $R^3$, $R^4$ and $R^5$ can be converted by conventional methods into different groups included within those previously defined, if desired, at the end or at any stage of the process above. This conversion or masking/unmasking of the protecting groups are well known in cephalosporin area (see, e.g. "Cephalosporins and Penicillins", E. H. Flynn Ed.).

The potentialities of protease inhibitor therapy in the treatment of conditions resulting from the destruction of connective tissues have recently received particular attention. Much effort has been devoted to the search for inhibitors of human leukocyte elastase (HLE), which is the primary destructive agent in pulmonary emphysema and is probably involved in rheumatoid arthritis (J. C. Power, Am. Rev. Resp. Diseases 127, S54–S58, 1983; C. H. Hassal et al, FEBS Letters, 183, n. 2, 201, 1985, G. Weinbaum and V. V. Damiano, TIPS, 8, 6, 1987; M. Velvart, Rheumatol. Int. 1, 121, 1981). Low molecular weight inhibitors appear to have a number of advantages over natural high molecular weight protease inhibitors from either plant or animal sources: 1) they can be obtained in quantities; 2) they can be rationally designed or optimised; 3) they are not antigenic; and 4) they may be used orally or in aerosols. Many low molecular weight elastase inhibitors discovered so far contain reactive functional groups (chloromethyl ketones, isocyanates, etc); they may react with functional groups of proteins, and therefore they may be quite toxic. In this respect, β-lactam compounds are of potential interest because, though reactive towards serine protease, they are, as it is known, non-toxic at very high concentrations. The compounds of the present invention are characterized by high inhibitory activity on elastases, especially human leukocyte elastase (HLE). In particular, the simultaneous introduction of two substituents $R_4$ and $S(=O)_nR_5$, as herein described, at the C-2 position of the cephem nucleus resulted in an unpredictable enhancement of inhibitory activity, relative to the corresponding compounds unsubstituted at C-2 (e.g., Reference Compound 1 in Table 2), which are disclosed in our patent U.S. 5,077,286 (Dec. 31, 1991). In most cases, such compounds proved also more active than the corresponding compounds carrying a single $S(=O)_nR_5$ substituent at C-2 (e.g., Reference Compound 2 in Table 2), which are disclosed in our patent application WO 91/09036, published Jun. 27, 1991.

In fact, when tested as inhibitors of human leukocyte elastase (HLE), representative compounds of formula (I) showed high "potency" (low value of apparent dissociation constant of the HLE-inhibitor complex at steady state, $K_i^{ss}$) and high "efficiency" (high value of rate of formation of the HLE-inhibitor complex, $K_5/K_i$):

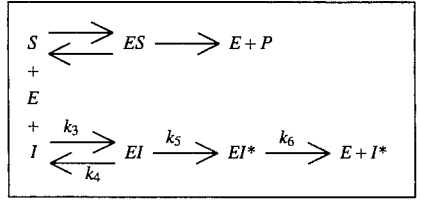

$K_I = k_4/k_3$    $K_I^{SS} = K_I \dfrac{k_6}{(k_5 + k_6)}$ wherein
E=enzyme (HLE)
S=substrate (see Protocol)
P=product (see Protocol)
I=inhibitor
EI=Michaelis complex
EI*=covalent complex (inactivated enzyme)
I*=inactivated inhibitor To illustrate this point, Table 2 reports such parameters for representative compounds within the present invention, and reference compounds of previous art.

Table 2 incorporates, as a further meaningful reference, the corresponding data obtained for L-659,286, another β-lactam compound which was recently reported to undergo preclinical studies for the treatment and control of pulmonary emphysema (Am. Rev. Respir. Dis. 1988, 137, 204; Agents and Actions, 1988, 25, 60; Journal of Cellular Biochemistry 1989, 39, 47–53, J. Med. Chem. 1992, 35, 3731–3744), independently synthesized in our laboratories.

TABLE 2

| Compound[a] | $K_I^{ss}$ (nM) | $K_5/K_I$ (M$^{-1}$S$^{-1}$) |
|---|---|---|
| 5 | 1.9 | 570,000 |
| 6 | 1.0 | 600,000 |
| 7 | 3.0 | 360,000 |
| 10 | 4.0 | 110,000 |
| 11 | <1 | 13,000,000 |
| 12 | 30 | 37,000 |
| 15 | ND | 1,400,000 |
| 18 | 16 | 14,000 |
| 24 | 8.0 | 93,000 |
| 28 | 3.0 | 1,400,000 |
| 30 | 1.0 | 77,000 |
| 31 | 1.3 | 560,000 |
| 32 | 7.0 | 200,000 |
| 46 | 4.0 | 160,000 |
| Ref. 1[b] | 1,300 | 90 |
| Ref. 2[c] | 93 | 26,000 |
| Ref. 3[d] | 140 | 1,500 |

[a] Compound numbers refers to respective numbers of Table 1
[b] 2-Unsubstituted compound, formula below, US Pat. No. 5,077,286, example 2
[c] 2-Monosubstituted compound, formula below, Pat. Appl. WO 91/09036, example 13
[d] Merck L-659,286, formula below, cited references Formulae of reference compounds:

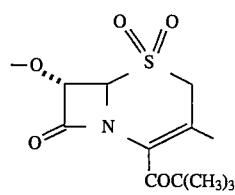

Reference Compound 1

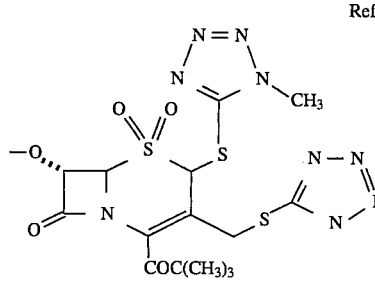

Reference Compound 2

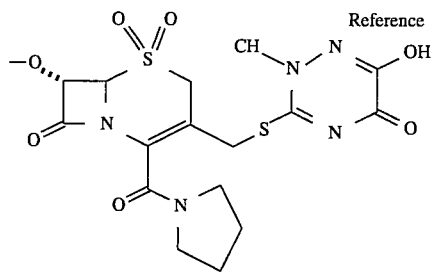

Reference Compound 3

Protocol

Kinetic parameters of HLE (Calbiochem) were determined at 37° C., 0.027M pH 7.4 phosphate buffer, 1% DMSO, 1% MeCN, NaCl (I=0.15), by monitoring the release of 7-amino-4-methylcoumarin (fluorescence detection) from N-methoxysuccinyl-alanyl-prolyl-valyl-7-amido-4-methylcoumarin as the substrate, according to the equations:

$$[P] = V_s t + \frac{V_z - V_s}{K}(1 - e^{kt})$$

$$K = K_6 + K_5 \frac{[I]/K_I}{1 + [S]/K_m + [I]/K_I}$$

$$V_s = V_o \frac{1 + [S]/K_m}{1 + [S]/K_m + [I]/K_I^{ss}}$$

wherein

[P], [I], [S]=product, inhibitor, and substrate concentration $V_s$=steady state rate $V_z$=zero time rate $V_o$=rate at [I]=0

$K_m$=Michaelis constant for the enzyme substrate pair (independently determined under the same experimental conditions)

Full details of the Experimental Protocol are reported in M. Alpegiani et al., Eur. J. Med. Chem. 1992, 27, 875–890.

Owing to their high elastase-inhibiting activity and their quite negligible toxicity, (the orientative acute toxicity by i.v., oral or aerosol route is almost always greater than 500 mg/kg in rat) the compounds of the present invention can be used in the treatment of inflammatory and degenerative diseases caused by proteolytic enzymes in mammals including humans. The compounds can be used to make medicaments useful to prevent or arrest the progression of diseases caused by proteolytic degradation of lungs and connective tissues, reduce inflammation and fever, and relieve pain. Such diseases are emphysema, acute respiratory distress syndrome, bronchial inflammation, rheumatoid arthritis, osteoarthritis, infectious arthritis, rheumatic fever, spondylitis, gout, lupus, psoriasis, and the like.

Accordingly, the present invention also provides pharmaceutical and veterinary compositions containing a suitable carrier and/or diluent and, as an active principle, a 4-acyl-cephem sulphone of formula I or a pharmaceutically or veterinarily acceptable salt thereof. The pharmaceutical or veterinary compositions containing a compound of formula I or salt thereof may be prepared in a conventional way by employing conventional non-toxic pharmaceutical carriers or diluents in a variety of dosage forms and ways of administration. In particular, the compounds of formula I can be administered:

A)

Orally, for example, as tablets, troches, lozenges, aqueous or oily suspensions, dispersible powders or granules, emulsions, hard or soft capsules, or syrups or elixirs.

Compositions intended for oral use may be prepared according to any method known in the art for the manufacture of pharmaceutical compositions and such compositions may contain one or more agents selected from the group consisting of sweetening agents, flavoring agents, coloring agents and preserving agents in order to provide pharmaceutically elegant and palatable preparations.

Tablets contain the active ingredient in admixture with non-toxic pharmaceutically acceptable excipients which are suitable for the manufacture of tablets.

These excipients may be for example, inert diluents, such as calcium carbonate, sodium carbonate, lactose, calcium phosphate or sodium phosphate; granulating and disintegrating agents, for example, maize starch, or alginic acid; binding agents, for example starch, gelatin or acacia, and lubricating agents, for example magnesium stearate, stearic acid or talc.

The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed.

Formulation for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin, or olive oil.

Aqueous suspensions contain the active materials in admixture with excipients suitable for the manufacture of aqueous suspensions.

Such excipients are suspending agents, for example, sodium carboxymethylcellulose, methylcellulose, hydroxypropylmethylcellulose, sodium alginate, polyvinylpyrrolidone gum tragacanth and gum acacia; dispersing or wetting agents may be naturally-occurring phosphatides, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan monooleate. The said aqueous suspensions may also contain one or more preservatives, for example, ethyl or n-propyl p-hydroxybenzoate one or more coloring agents, one or mere flavoring agents, or one or more sweetening agents, such as sucrose or saccharin. Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents, such as those set forth above, and flavouring agents may be added to provide a palatable oral preparation. These compositions may be preserved by the addition of an antioxidant such as ascorbic acid. Dispersible powders and granules suitable for preparation of an aqueous suspension by the addition of water provide the active ingredient in admixture with a dispersing or wetting agent, a suspending agent and one or more preservatives.

Suitable dispersing or wetting agents and suspending agents are exemplified by those already mentioned above.

Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example glum acacia or gum tragacanth, naturally-occurring phosphatides, for example soy bean, lecithin, and esters or partial esters derived from fatty acids and hexitol anhydrides, for example sorbitan mono-oleate, and condensation products of the said partial esters with ethylene oxide, for example polyoxyethylene sorbitan monooleate. The emulsion may also contain sweetening and flavoring agents.

Syrups and elixirs may be formulated with sweetening agents, for example glycerol, sorbitol or sucrose.

Such formulations may also contain a demulcent, a preservative and flavoring and coloring agents.

B)

Parenterally, either subcutaneously, or intravenously, or intramuscularly, or intrasternally, or by infusion techniques, in the form of sterile injectable aqueous or olagenous suspensions. The pharmaceutical compositions may be in the form of a sterile injectable aqueous or olagenous suspension.

This suspension may be formulated according to the known art using those suitable dispersing of wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium.

For this purpose any bland fixed oil may be employed including synthetic mono- or diglycerides. In addition fatty acids such as oleic acid find use in the preparation of injectables;

C)

By inhalation, in the form of aerosols or solutions for nebulizers;

D)

Rectally in the form of suppositories prepared by mixing the drug with a suitable non-irratating excipient which is solid at ordinary temperature but liquid at the rectal temperature and will therefore melt in the rectum to release the drug. Such materials are cocoa butter and poly-ethylene glycols;

E)

Topically, in the form of creams ointments, jellies, solutions or suspensions.

Still a further object of the present invention is to provide a method of controlling inflammatory and degenerative diseases by administering a therapeutically effective amount of one or more of the active compounds encompassed by the formula I in humans or mammalians in need of such treatment. Daily dose are in the range of about 0.1 to about 50 mg per kg of body weight, according to the activity of the specific compound, the age, weight and conditions of the subject to be treated, the type and severity of the disease, and the frequency and route of administration; preferably, daily dosage levels for humans are in the range of 20 mg to 2 g. The amount of active ingredient that may be combined with the carrier materials to produce a single dosage form will vary depending upon the host treated and the particular mode of administration. For example, a formulation intended for the oral administration to humans, may contain from 5 mg to 2 g of active agent compounded with an appropriate and convenient amount of carrier material which may vary from about 5 to about 95 percent of the total composition. Dosage unit forms will generally contain between from about 5 mg to about 500 mg of active ingredient.

Compounds of formula (II) are known or can be prepared from known compounds as described in our PCT patent application WO91/09036. Compounds of formula (III) are known compounds or can be prepared from known compounds by known methods.

EXAMPLE 1

4-tert-Butylcarbonyl-2,3-dimethyl-7α-methoxy-2-(1-methyl-1,2,3,4-tetrazol-5-yl)thio-3-cephem 1,1-dioxide (compound 5)

A solution of 4-tert-butylcarbonyl-7α-methoxy-3-methyl-2-(1-methyl-1,2,3,4-tetrazol-5-yl)thio-3-cephem 1,1-dioxide (300 mg), prepared as described in PCT EP 90/02189 in dimethyl sulphoxide (3 ml), was treated at room temperature with triethylamine (0.110 ml) and methyl iodide (0.135 ml). After 1 hr, the reaction mixture was diluted with ethyl acetate, sequentially washed with a dilute solution of hydrochloric acid and brine and eventually dried over $Na_2SO_4$. Removal of the solvent and flash chromatography of the residue afforded the title compound as a white solid (160 mg).

m.p.: 180°–5° C. (decomp.).

IR (KBr) $v_{max}$ 1800, 1700 cm$^{-1}$ $^1$H-nmr (200 MHz, CDCl$_3$): δ1.24 (9H,s), 1.80 (3H,s), 1,83 (3H,s), 3.56 (3H,s), 4.16 (3H,s), 5.19 (1H,d,J=1.7 Hz), 5.27 (1H,d,J=1.7 Hz) ppm.

EXAMPLE 2

2-Benzyl-4-tert-butylcarbonyl-7α-methoxy-3-methyl-2-(1-methyl-1,2,3,4-tetrazol-5-yl)thio-3-cephem 1,1-dioxide (compound 10)

415 mg of 4-tert-butylcarbonyl-7α-methoxy-3-methyl-2-(1-methyl-1,2,3,4-tetrazol-5-yl)thio-3-cephem 1,1-dioxide was dissolved in dimethyl sulphoxide (3 ml) and triethylamine (0.153 ml) and benzyl bromide (0.360 ml) were added. The reaction mixture was left overnight at room temperature, diluted with ethyl acetate, washed with a dilute solution of hydrochloric acid and eventually with brine. Drying over $Na_2SO_4$ and removal of the organic solvent left a residue which was then purified by flash chromatography affording the title compound as a white solid (270 mg).

m.p.: 63°–5° C.

IR (KBr) $v_{max}$ 1800, 1700 cm$^1$.

$^1$H nmr (200 MHz, CDCl$_3$): δ1.22 (9H,s), 1.81 (3H,s), 3.46 and 3.97 (1H,each d,J=15 Hz), 3.48 (3H,s), 4.05 (3H,s), 4.81 (1H,d,J=1.6 Hz), 5.20 (1H,d,J=1.6 Hz), 7.34–7.55 (5H,m) ppm.

EXAMPLE 3

4-tert-Butylcarbonyl-2-tert-butyloxycarbonylmethyl-7α-methoxy-3-methyl-2-(1-methyl-1,2,3,4-tetrazol-5-yl)thio-3-cephem 1,1-dioxide (compound 8)

A solution of tert-butylcarbonyl-7α-methoxy-3-methyl-2-(1-methyl-1,2,3,4-tetrazol-5-yl)thio-3-cephem 1,1-dioxide (120 mg) in dimethyl sulphoxide (1 ml) was treated, at room temperature, with triethylamine (0.044 ml) and tert-butyl-bromoacetate (0.127 ml). After 2 hrs, the reaction mixture was diluted with ethyl acetate, washed with 1N hydrochloric acid and with brine and eventually dried over $Na_2SO_4$. The pure title compound was obtained as a yellowish solid after removal of the organic solvent and flash chromatography (50 mg).

m.p.: 71°–3° C.

IR (KBr) $v_{max}$ 1800, 1740, 1700 cm$^{-1}$.

$^1$H nmr (200 MHz, CDCl$_3$): δ1.26 (9H,s), 1.44 (9H,s), 1.90 (3H,s), 2.94 and 3.38 (1H,each d,J=16.6 Hz), 3.55 (3H,s), 4.15 (3H,s), 5.19 (1H,d,J=1.7 Hz), 5.28 (1H,d,J=1.7 Hz) ppm.

EXAMPLE 4

4-tert-Butylcarbonyl-7α-methoxy-3-methyl-2-(1-methyl-1,2,3,4-tetrazol-5-yl)thio-2-(4-nitrobenzyl)-3-cephem 1,1-dioxide (compound 6)

A solution of 4-tert-butylcarbonyl-7α-methoxy-3-methyl-2-(1-methyl-1,2,3,4-tetrazol-5-yl)thio-3-cephem 1,1-dioxide (120 mg) and 4-nitro-benzyl bromide (187 mg) in dimethyl sulphoxide (1 ml) was treated with triethylamine (0.048 ml) and left overnight at room temperature. Then the reaction mixture was poured into water and extracted with ethyl acetate. Drying over $Na_2SO_4$, removal of the solvent and flash chromatography of the crude residue afforded the title compound as a white solid (70 mg).

m.p.: 76°–80° C.

IR(KBr) $v_{max}$ 1800, 1700 cm$^1$.

$^1$H nmr (200 MHz, CDCl$_3$): δ1.23 (9H,s), 1.83 (3H,s), 3.48 (3H,s), 3.57 and 4.02 (1H,each d, J=15.2 Hz). 3.48 (3H,s), 4.09 (3H,s), 4.76 (1H,d,J=1.6 Hz), 5.19 (1H,d,J=1.6 Hz), 5.19 (1H,d,J=1.6 Hz), 7.70, 8.22 (4H,each d,J=8.8 Hz) ppm.

EXAMPLE 5

2-Allyl-4-tert-butylcarbonyl-7α-methoxy-3-methyl-2-(1-methyl-1,2,3,4-tetrazol-5-yl)thio-3-cephem 1,1-dioxide (compound 7)

A solution of 4-tert-butylcarbonyl-7α-methoxy-3-methyl-2-(1-methyl-1,2,3,4-tetrazol-5-yl)thio-3-cephem 1,1-dioxide (100 mg) and allyl bromide (0.061 ml) was treated, at room temperature, with triethylamine (0.037 ml). After 2 hrs the reaction was over (TLC monitoring). Dilution with dichloromethane, washing with brine, drying over $Na_2SO_4$ and removal of the solvent left a residue which afforded the title compound as a white solide (60 mg) after flash chromatography.

m.p.: 120°–3° C.

IR (KBr) $v_{max}$ 1800, 1700 cm$^{-1}$.

$^1$H nmr (200 MHz, CDCl$_3$): δ1.22 (9H,s), 1.78 (3H,s), 2.89–3.32 (2H,m), 3.52 (3H,s), 4.13 (3H,s), 5.00 (1H,d,J= 1.6 Hz), 5.19 (1H,d,J=1.6 Hz), 5.27 –5.37 (2H,m), 5.93–6.10 (1H,m) ppm.

EXAMPLE 6

2-(6-Benzhydryloxy-2-methyl-5-oxo-2,5-dihydro-1,2,4-triazin-3-yl)thio-4-tert-butylcarbonyl-2,3-dimethyl-7α-methoxy-3-cephem 1,1-dioxide (compound 11)

A solution of 2-(6-benzhydryloxy-2-methyl-5-oxo-2,5-dihydro-1,2,4-triazin-3-yl)thio-4-tert-butylcarbonyl-7α-methoxy-3-methyl-3-cephem 1,1-dioxide (550 mg), prepared as described in PTC EP 90/02189 in dimethyl sulphoxide (4 ml) was treated with methyl iodide (0.170 ml) and triethylamine (0.147 ml). After 2 hrs the reaction was diluted with dichloromethane, washed in sequence with hydrochloric acid and brine, and dried $Na_2SO_4$. Removal of the solvent and flash chromatography of the crude residue gave the title compound (300 mg) as a yellowish solid.

m.p.: 175°–9° C. (decomp.).

IR (KBr) $v_{max}$ 1800, 1700, 1675 cm$^{-1}$.

$^1$H nmr (200 MHz, CDCl$_3$): δ1.26 (9H,s), 1.70 (3H,s), 1.82 (3H,s), 3.56 (3H,s), 3.62 (3H,s), 5.35 (1H,d,J=1.6 Hz), 6.10 (1H,d,J=1.6 Hz), 6.73 (1H,s), 7.29–7.45 (10H,m) ppm.

EXAMPLE 7

2-(6-benzhydryloxy-2-methyl-5-oxo-2,5-dihydro-1,2,4-triazin-3-yl)thio-2-benzyl-4-tert-butylcarbonyl-7α-methoxy-3-methyl-3-cephem 1,1-dioxide (compound 14)

A solution of 2-(6-benzhydryloxy-2-methyl-5-oxo-2,5-dihydro-1,2,4-triazin-3-yl)thio-4-tert-butylcarbonyl-7α-methoxy-3-methyl-3-cephem 1,1-dioxide (300 mg) in acetonitrile (5 ml) was treated at room temperature with triethylamine (0.067 ml) and benzyl bromide (0.172 ml). After 4 hr, the reaction mixture was diluted with dichloromethane, washed with brine and dried over Na$_2$SO$_4$. The solvent was then removed and the residue purified by flash chromatography, thereby obtaining the title compound as a white solid (180 mg).

m.p.: 175°–8° C. (decomp.).

IR (KBr) $v_{max}$ 1790, 1700, 1670 cm$^1$.

$^1$H nmr (200 MHz, CDCl$_3$): δ1.30 (9H,s), 1.57 (3H,s), 3.6 (6H,s), 3.40 and 3.84 (1H,each d,J=14.9 Hz), 5.37 (1H,d,J=1.5 Hz), 5.9 (1H,d,J=1.5 Hz), 6.73 (1H,s), 7.32–7.48 (5H,m) ppm.

EXAMPLE 8

4-tert-Butylcarbonyl-7α-methoxy-2-methyl-2-(1-methyl-1,2,3,4-tetrazol-5-yl)thio-3-(1-methyl-1,2,3,4-tetrazol-5-yl)thiomethyl-3-cephem 1,1-dioxide (compound 28)

A solution of 4-tert-butylcarbonyl-7α-methoxy-2-(1-methyl-1,2,3,4-tetrazol-5-yl)thio-3-(1-methyl-1,2,3,4-tetrazol-5-yl)thiomethyl-3-cephem 1,1-dioxide (100 mg), prepared as described in PTC EP 90/02189 in acetonitrile (2 ml) was treated at room temperature with triethylamine (0.040 ml) and methyl iodide (0.060 ml). The reaction mixture was stirred for 30 minutes and the organic solvent completely removed in vacuo. The resulting crude residue was eventually taken up in dichloromethane and purified by flash chromatography affording the title compound as a yellowish solid (40 mg).

m.p.: 71°–3° C.

Ir (KBr) $v_{max}$ 1700, 1800 cm$^{-1}$.

$^1$H nmr (200 MHz, CDCl$_3$) δ1.24 (9H,s), 2.03 (3H,s), 3.56 (3H,s), 3.90 (3H,s), 4.19 (3H,s), 3.70 and 4.38 (2H,each d,J=14 Hz), 5.25 (2H,s) ppm.

EXAMPLE 9

2-(4-allyloxycarbonylbenzyl)-4-tert-butylcarbonyl-7α-methoxy-3-methyl-2-(1-methyl-1,2,3,4-tetrazol-5-yl)thio-3-cephem 1,1-dioxide (compound 31)

4-tert-Butylcarbonyl-7α-methoxy-3-methyl-2-(1-methyl-1,2,3,4-tetrazol-5-yl)thio-3-cephem 1,1-dioxide (200 mg) was dissolved in dimethylsulphoxide (2 ml). Triethylamine (0.074 ml) and allyl 4-bromomethyl benzoate (390 mg) were added at room temperature. After about 2 hrs, the reaction was over (TLC monitoring). The mixture was diluted with dichloromethane, washed with brine and dried over Na$_2$SO$_4$. Removal of the solvent and flash chromatography afforded the title compound as a white solid (90 mg).

m.p.: 73°–5° C.

IR (KBr): $v_{max}$ 1800, 1725, 1700 cm$^{-1}$.

$^1$H nmr (200 MHz, CDCl$_3$) δ1.22 (9H,s), 1.82 (3H,s), 3.47 (3H,s), 4.06 (3H,s), 3.51 and 4.00 (2H,each d,J=16.1 Hz), 4.79 (1H,d,J=1.6 Hz), 4.79–4.83 (2H,m), 5.19 (1H,d, J=1.6 Hz), 5.25–5.45 (2H,m), 5.95–6.09 (1H,m), 7.61 and 8.05 (2H, each d, J=8.3 Hz) ppm.

EXAMPLE 10

2-(4-benzhydryloxycarbonylbenzyl)-4-tert-Butylcarbonyl-7α-methoxy-3-methyl-2-(1-methyl-1,2,3,4-tetrazol-5-yl)thio-3-cephem1,1-dioxide (compound 30)

A solution of 4-tert-butylcarbonyl-7α-methoxy-3-methyl-2-(1-methyl-1,2,3,4-tetrazol-5-yl)thio-3-cephem 1,1-dioxide (500 mg) in dimethyl sulphoxide (4 ml) was treated at room temperature with triethylamine (0.185 ml) and benzhydryl-4-bromomethylbenzoate (1.4 g). The solution was stirred for 1 hr, diluted with dichloromethane, washed with brine and eventually dried over Na$_2$SO$_4$. Removal of the solvent left a crude residue which afforded the title compound as a yellowish solid (250 mg) after flash chromatography.

m.p.: 76°–80° C.

IR (KBr) $v_{max}$ 1800, 1725, 1700 cm$^{-1}$. (3H,s), 3.55 and 4.05 (1H,each d,J=16.1 Hz), 4.79 (1H,d,J=1.5 Hz), 5.23 (1H,d,J=1.5 Hz), 7.1 (1H,s), 7.3–7.48 (5H,m), 7.66 and 8.16 (4H,each d,J=8.4 Hz ) ppm.

EXAMPLE 11

2-(2,5-Dihydro-6-hydroxy-2-methyl-5-oxo-1,2,4-triazin-3-yl)thio-4-tert-butylcarbonyl-2,3-dimethyl-7α-methoxy-3-methyl-3-cephem 1,1-dioxide (compound 12)

A solution of 2-(2,5-dihydro-6-hydroxy-2-methyl-5-oxo-1,2,4-triazin-3-yl)thio-4-tert-butylcarbonyl-7α-methoxy-3-methyl-3-cephem 1,1-dioxide (460 mg) in dry THF (10 ml) was sequentially treated with tert-butyldiphenylsilyl chloride (0.27 ml) and triethylamine (0.15 ml). After stirring 15 minutes at room temperature the reaction mixture was partitioned between EtOAc and water. The upper layer was dried (Na$_2$SO$_4$) and concentrated. Upon treatment of the residue with diisopropyl ether a white solid was formed, which was filtered and dried under vacuum. The obtained white powder (600 mg) was shown to correspond to 2-(6-tert-butyldiphenylsilyloxy-2,5-dihydro-2-methyl-5-oxo-1,2,4-triazin-3-yl)thio-4-tert-butyl-carbonyl-7α-methoxy-3-methyl-3-cephem 1,1-dioxide. A portion of this product (170 mg) was dissolved in dry CH$_3$CN (3 ml) and treated with methyl iodide (0.15 ml) and triethylamine (0.05 ml). The resulting mixture was stirred at room temperature for 4 hours, then concentrated under vacuum. Flash chromatography of the residue (eluting with diisopropyl ether/chloroform 1:1) gave 2-(6-tert-butyldiphenylsilyloxy-2,5-dihydro-2-methyl-5-oxo-1,2,4-triazin-3-yl)thio-4-tert-butylcarbonyl-2,3-dimethyl-7α-methoxy-3-cephem 1,1-dioxide as the first eluted product (150 mg). A solution of this product in EtOH (5 ml) and AcOH (2 ml) was left stand at room temperature overnight, then rotoevaporated to give a final volume of about 0.5 ml. Upon treatment with diethyl ether, the title product was obtained as a white powder (80 mg).

IR (KBr) 1765, 1700, 1650 cm$^{-1}$.

NMR (200 MHz, CDCl$_3$): 1.26 (9H,s), 1.74 (3H,s), 1.87 (3H,s), 3.56(3H,s), 3.76 (3H,s), 5.32 (1H,d,J=1.6 Hz), 5.89 (1H,d,J=1.6 Hz) ppm.

EXAMPLE 12

2-Benzyl-2-(2,5-dihydro-6-hydroxy-2-methyl-5-oxo-1,2,4-triazin-3-yl)thio-4-tert-butylcarbonyl-7α-methoxy-3-methyl-3-cephem 1,1-dioxide
(compound 18)

A mixture of 2-(6-tert-butyldiphenylsilyloxy-2,5-dihydro-2-methyl-5-oxo-1,2,4-triazin-3-yl)thio-4-tert-butylcarbonyl-7α-methoxy-3-methyl-3-cephem 1,1-dioxide (360 mg) (prepared as described in Example 11), benzyl bromide (0.185 ml) and triethylamine (0.11 ml) in CH$_3$CN (6 ml) was stirred at room temperature overnight. Removal of the solvent and chromatography ( SiO$_2$, eluting with EtOAc/n-hexane mixtures) of the residue allowed the isolation of 2-benzyl-2-(6-tert-butyldiphenylsilyloxy-2,5-dihydro-2-methyl-5-oxo-1,2,4-triazin-3-yl)thio-4-tert-butylcarbonyl-7α-methoxy-3-methyl-3-cephem 1,1-dioxide as a white powder (210 rag). This product was dissolved acetic acid (2 ml), treated with water (1 ml) anf silica gel (0.1 g) and stirred at room temperature for 40 hours. After concentration under reduced pressure, the residue was dissolved in the minimum amount of 4% aqueous NaHCO$_3$ and passed through a short pad of C-18 LiChroprep silica gel eluting with water then water-CH$_3$CN mixtures. Following lyophilization of the product containing fractions, the sodium salt of the title product was obtained as a light yellow powder. IR (KBr) 1795, 1700, 1655, 1615 cm$^{-1}$. NMR (200 MHz, D$_2$O): 1.08 (9H,s), 1.86 (3H,s), 3.58 (3H,s), 3.76 (1H,d,J=18 Hz), 3.86 (1H,d,J=18 Hz), 3.87 (3H,s), 5.51 (1H,d,J=1.1 Hz), 6.72 (1H,d,J=1.1 Hz), 7.3–7.7 (5H,m) ppm.

Mere partitioning of this sodium salt between 0.5N hydrochloric acid and EtOAc, separation of the organic phase, drying over Na$_2$SO$_4$ and removal of the solvent gave the title product as a white solid.

NMR (200 MHz, CDCl$_3$): 1.26 (9H,s), 1.61 (3H,s), 3.40 (1H,d,J=15 Hz), 3.56(3H,s), 3.69 (3H,s), 3.83 (1H,d,J=15 Hz), 5.30 (1H,d,J=1.6 Hz), 5.69 (1H,d,J=1.6 Hz), 7.3–7.5 (5H,m) ppm.

EXAMPLE 13

2-(2,5-Dihydro-6-methoxy-2-methyl-5-oxo-1,2,4-triazin-3-yl)thio-4-tert-butylcarbonyl-2,3-dimethyl-7α-methoxy-3-cephem 1,1-dioxide
(compound 15)

A solution of 2-(2,5-dihydro-6-hydroxy-2-methyl-5-oxo-1,2,4-triazin-3-yl)thio-4-tert-butylcarbonyl-7α-methoxy-3-methyl-3-cephem 1,1-dioxide (230 mg) in dry CH$_3$CN (10 ml) was sequentially treated with methyl iodide (0.8 ml) and triethylamine (0.15 ml). After stirring 20 hours at room temperature the reaction mixture was partitioned between EtOAc and water. The upper layer was dried (Na$_2$SO$_4$) and concentrated. Upon purification of the residue by flash chromatography the title product was obtained as a white powder.

IR (KBr) 1790, 1705, 1675 cm$^{-1}$.

NMR (200 MHz, CDCl$_3$): 1.26 (9H,s), 1.73 (3H,s), 1.85 (3H,s), 3.56 (3H,s), 3.73 (3H,s), 3.90 (3H,s), 5.36 (1H,d,J=1.7 Hz), 6.09 (1H,d,J=1.7 Hz) ppm.

EXAMPLE 14

2-Benzyl-2-(6-benzyloxy-2,5-dihydro-2-methyl-5-oxo-1,2,4-triazin-3-yl)thio-4-tert-butylcarbonyl-7α-methoxy-3-methyl-3-cephem 1,1-dioxide
(compound 46)

Using a procedure similar to that described in Example 13 and substituting benzyl bromide for methyl iodide the title product was obtained as a waxy solid.

NMR (260 MHz, CDCl$_3$): 1.25 (9H,s), 1.62 (3H,s), 3.38 (1H,d,J=15 Hz), 3.54 (3H,s), 3.65 (3H,s), 3.81 (1H,d,J=15 Hz), 5.18 (2H,ABq), 5.34 (1H,d,J=1.5 Hz), 5.91 (1H,d,J=1.5 Hz), 7.2–7.8 (10H,m) ppm.

EXAMPLE 15

4-tert-Butylcarbonyl-2-(4-carboxybenzyl)-7α-methoxy-3-methyl-2-(1-methyl-1,2,3,4-tetrazol-5-yl)thio-3-cephem 1,1-dioxide
(compound 32)

A solution of 2-(4-benzhydryloxycarbonylbenzyl)-4-tert-butyl-carbonyl-7α-methoxy-3-methyl-2-(1-methyl-1,2,3,4-tetrazol-5-yl)thio-3-cephem 1,1-dioxide (320 mg) in m-cresol (5 ml) was treated with trifluoroacetic acid (0.035 ml) and heated at 50° C. for 3 hours. The reaction mixture was cooled to room temperature then diluted with diethyl ether and treated with saturated aqueous NaHCO$_3$. The aqueous phase was rinsed with EtOAc, separated then covered with EtOAc and made acidic with 1N hydrochloric acid. The upper layer was dried (Na$_2$SO$_4$) and rotoevaporated to give the crude title product as a waxy solid (200 mg).

NMR (200 MHz, CDCl$_3$): 1.23 (9H,s), 1.83 (3H,s), 3.48 (3H,s), 3.54 (1H,d,J=15.2 Hz), 4.01 (1H,d,J=15.2 Hz), 4.07 (3H,s), 4.77 (1H,d,J=1.6 Hz), 5.20 (1H,d,J=1.6 Hz), 7.65 (2H,d,J=8.2 Hz), 8.08 (2H,d,J=8.2 Hz) ppm.

A portion of this product (100 mg) was dissolved in the minimum amount of 4% aqueous NaHCO$_3$ and passed through a short pad of C-18 LiChroprep silica gel eluting with water then water-CH$_3$CN mixtures. Following freeze-drying of the product containing fractions, the sodium salt of the title product was obtained as a white lyophile.

NMR (200 MHz, D$_2$O): 0.96 (9H,s), 1.67 (3H,s), 3.45 (3H,s), 3.73 (2H,ABq), 4.14 (3H,s), 5.49 (1H,d,J=1.4 Hz), 5.69 (1H,d,J=1.4 Hz), 7.46 (2H,d,J=8.2 Hz), 7.76 (2H,d,J=8.2 Hz) ppm.

EXAMPLE 16

2-allyl-2-(6-benzhydryloxy-2,5-dihydro-2-methyl-5-oxo-1,2,4-triazin-3-yl)thio-4-tert-butylcarbonyl-7α-methoxy-3-methyl-3-cephem 1,1-dioxide
(compound 24)

Following a procedure similar to that described in Example 7 and substituting allyl bromide for benzyl bromide the title product was obtained as a white solid.

IR (KBr) 1800, 1700, 1670 cm$^{-1}$.

NMR (200 MHz, CDCl$_3$): 1.25 (9H,s), 1.70 (3H,s), 2.8–3.1 (2H,m), 3.56(3H,s), 3.62 (3H,s), 5.2–5.4 (2H,m), 5.35 (1H,d,J=1.6 Hz), 5.9–6.1 (1H,m), 6.08 (1H,d,J=1.6Hz), 6.72 (1H,s), 7.2–7.5 (10H,m) ppm.

We claim:

1. A cephalosporin sulphone of the formula (I), or a pharmaceutically or veterinarily acceptable salt thereof:

wherein:

n is 0, 1 or 2;

$R_1$ is selected from the group consisting of hydrogen, fluorine, chlorine, methyl, ethyl, propyl, iso-propyl, n-butyl, 2-methyl-1-propyl, allyl, methylallyl, crotyl, 3-methyl-2-butene-1-yl, methoxy, ethoxy, propoxy, iso-propoxy, n-butoxy, methylthio, ethylthio, propylthio, isopropylthio, n-butylthio, formamido, acetamido and propionamido;

$R_2$ is selected from the group consisting of hydrogen, methyl, ethyl, propyl, iso-propyl, n-butyl, 2-methyl-1-propyl, neo-pentyl and 1,1-dimethylpropyl;

$R_3$ is selected from the group consisting of hydrogen, methyl, methoxymethyl, acetoxymethyl and the group—CH$_2$S—Het, wherein Het is selected from the group consisting of:

wherein $R^1$ is hydrogen, C$_1$–C$_5$-alkyl, C$_2$–C$_5$-alkenyl, phenyl, benzhydro or benzyl or a hydroxy protecting group, and $R^{IV}$ is hydrogen, C$_1$–C$_5$-alkyl, C$_2$–C$_5$-alkenyl, phenyl, benzhydryl, benzyl or a carboxy protecting group;

$R_4$ is selected from the group consisting of ethyl, methallyl, crotyl, methoxy carbonylmethyl, tert-butoxy carbonylmethyl, carboxymethyl, cyanomethyl, acetonyl, methoxymethyl, methoxyethoxymethyl, acetoxymethyl, benzyl, 4-methoxybenzyl, 4-nitrobenzyl, benzhydryl or a group of the formula:

$R_5$ is an unsubstituted or substituted C$_6$–C$_{10}$-aryl or a heterocyclyl group; said substituents being selected from the group consisting of:

C$_1$–C$_5$-alkyl;

C$_2$–C$_5$-alkenyl;

phenyl;

benzyl;

C$_3$–C$_6$-cycloalkyl;

halo;

protected hydroxy;

oxo;

cyano;

nitro;

azido;

protected amino or —NHR$^I$; or —NR$^I$R$^{II}$, wherein R$^I$ and R$^{II}$;

are the same or different, and are each hydrogen or C$_1$–C$_5$-alkyl, C$_2$–C$_5$-alkenyl, phenyl, benzhydryl or benzyl, or R$^I$ and R$^{II}$, taken together with the nitrogen atom, constitute a succinimido or phthalimido group;

protected carboxy;

—OR$^I$ or —OCH$_2$CH$_2$OR$^I$, wherein R$^I$ is as defined above;

—SR$^I$, wherein R$^I$ is as defined above;

—S(O)R$^I$, wherein R$^I$ is as defined above;

—S(O)$_2$R$^I$, wherein R$^I$ is as defined above;

a group of the formula —(CH$_2$)$_m$—COR$^I$, —COOR$^I$, —COO(CH$_2$)$_m$—COOR$^I$;

—S(CH$_2$)$_m$COOR$^I$, wherein R$^I$ is as defined above or COR$^{III}$, wherein R$^{III}$ is either R$^I$ as defined or fluoromethyl, trifluoromethyl or chloromethyl;

—OCOR$^{III}$, wherein R$^{III}$ is as defined above;

—CONH$_2$, —CONHR$^I$ or —CONHCH$_2$COOR$^I$, wherein R$^I$ is as defined above or —CONHCH$_2$COOH;

sulfo (SO$_3$H);

—NHCOR$^I$, wherein R$^I$ is as defined above;

—NHS(O)$_2$R$^I$, wherein R$^I$ is as defined above; and guanidino (—NHC(=NH)NH$_2$);

said heterocyclyl group being a 5- or 6-membered, saturated or unsaturated, heterocyclic ring selected from the group consisting of:

-continued

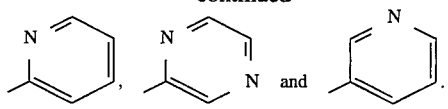

said $C_6$–$C_{10}$ aryl being selected from the group consisting of phenyl and naphthyl.

2. The compound of claim 1, wherein $R_5$ is phenyl, 4-carboxyphenyl or a heterocyclic ring of the formula:

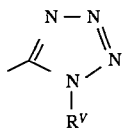

wherein $R^V$ is hydrogen, methyl, ethyl, propyl, phenyl, benzyl, carboxymethyl, 2-carboxyethyl, 3-carboxypropyl, 3-benzhydroxyloxycarbonylpropyl, 2-sulphoethyl, 2,2-dimethylaminoethyl; or

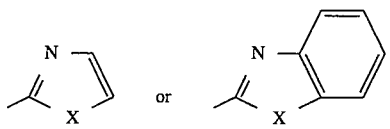

wherein X is oxygen, sulfur or —$NR^{VII}$, wherein $R^{VII}$ is hydrogen, methyl, phenyl, carboxymethyl;

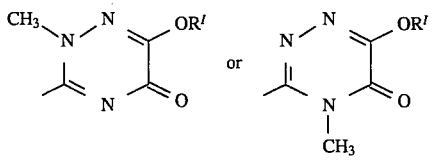

wherein $R^I$ is as defined above.

3. A pharmaceutical or veterinary composition, comprising a suitable carrier or diluent or both and, as an active principle, a compound according to claim 1 or a pharmaceutically or veterinarily acceptable salt thereof.

4. A method of treating an inflammatory or degenerative disease or both in a mammal caused by proteolytic enzymes, which comprises administrating one or more compounds of claim 1 to a mammal in need thereof.

5. The method of claim 4, wherein said mammal is a human.

6. The method of claim 4, wherein said compound is administered to said mammal in the treatment of a disease selected from the group consisting of emphysema, adult respiratory distress syndrome, rheumatic fever, spondylitis, gout, lupus or psoriasis.

* * * * *